United States Patent [19]

Kuris et al.

[11] 4,193,196

[45] Mar. 18, 1980

[54] FLUID SUPPLY UNIT FOR DENTAL INSTRUMENTS

[75] Inventors: Arthur Kuris, Riverdale; Leonard W. Suroff, Jerico, both of N.Y.

[73] Assignee: Aquasonic Products Corp., New York, N.Y.

[21] Appl. No.: 905,866

[22] Filed: May 15, 1978

Related U.S. Application Data

[63] Continuation-in-part of Ser. No. 843,416, Oct. 19, 1977, and Ser. No. 702,536, Jul. 6, 1976, abandoned.

[51] Int. Cl.² ............................................. A61C 19/02
[52] U.S. Cl. ...................................................... 433/82
[58] Field of Search ................ 32/22, 28, 58, DIG. 4; 310/84, 26

[56] References Cited

U.S. PATENT DOCUMENTS

| 3,077,665 | 2/1963 | Saltzman | 32/22 |
| 3,237,306 | 3/1966 | Staunt | 32/28 |
| 3,505,737 | 4/1970 | Merolla | 32/28 |
| 3,924,335 | 12/1975 | Balamuth et al. | 32/58 |

*Primary Examiner*—Robert Peshock
*Attorney, Agent, or Firm*—Watson, Leavenworth, Kelton & Taggart

[57] ABSTRACT

An auxiliary fluid supply unit that is adapted to be used in conjunction with commercially available professional dental and medical equipment to permit the user to select a variety of fluids to be administered to the patient during dental and other procedures.

46 Claims, 14 Drawing Figures

FLUID SUPPLY UNIT

FIG. 4 INTERCONNECTION OFF

OFF

INTERCONNECTION
OPERATE

FIG. 9 OPERATE

RINSE

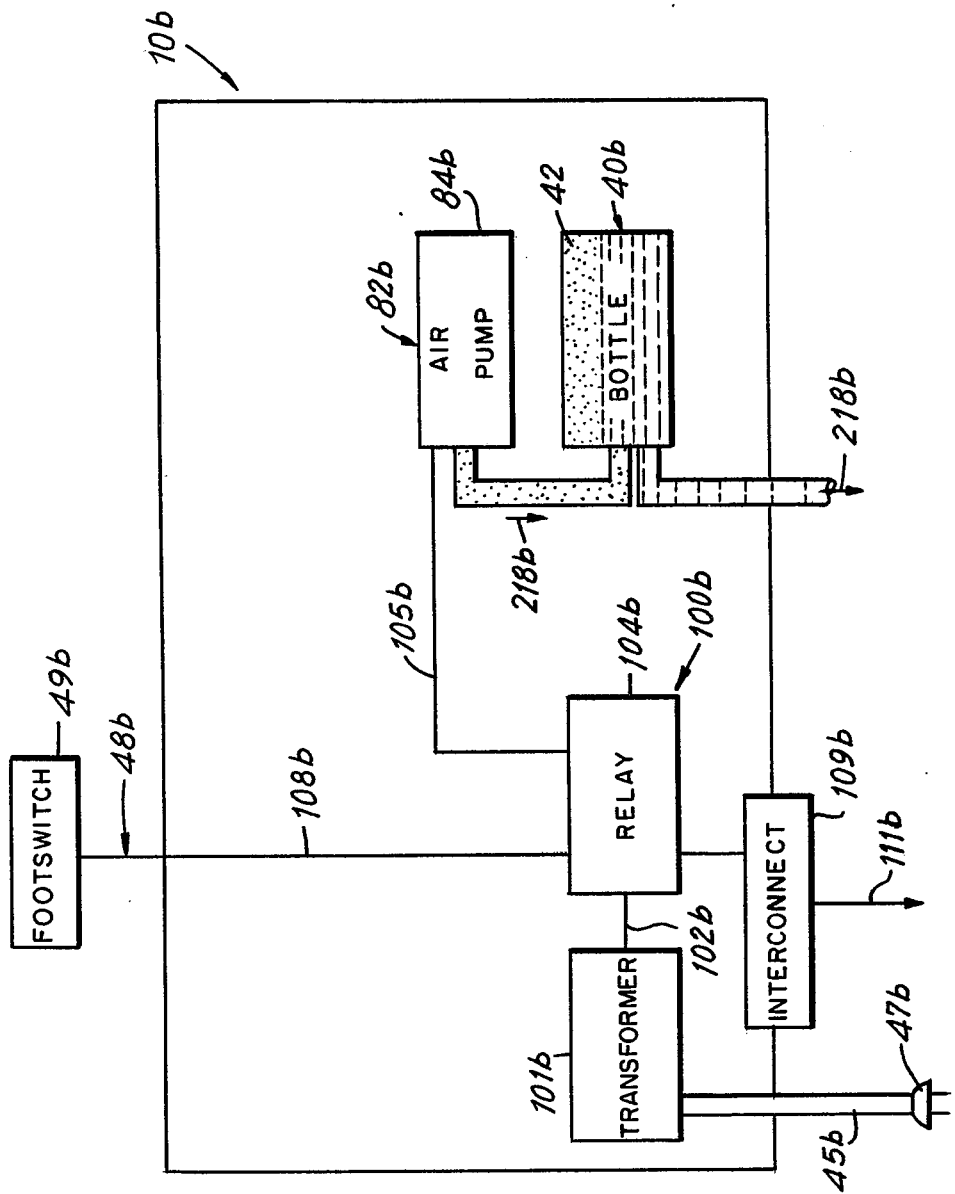
FIG. 13 FLUID SUPPLY UNIT

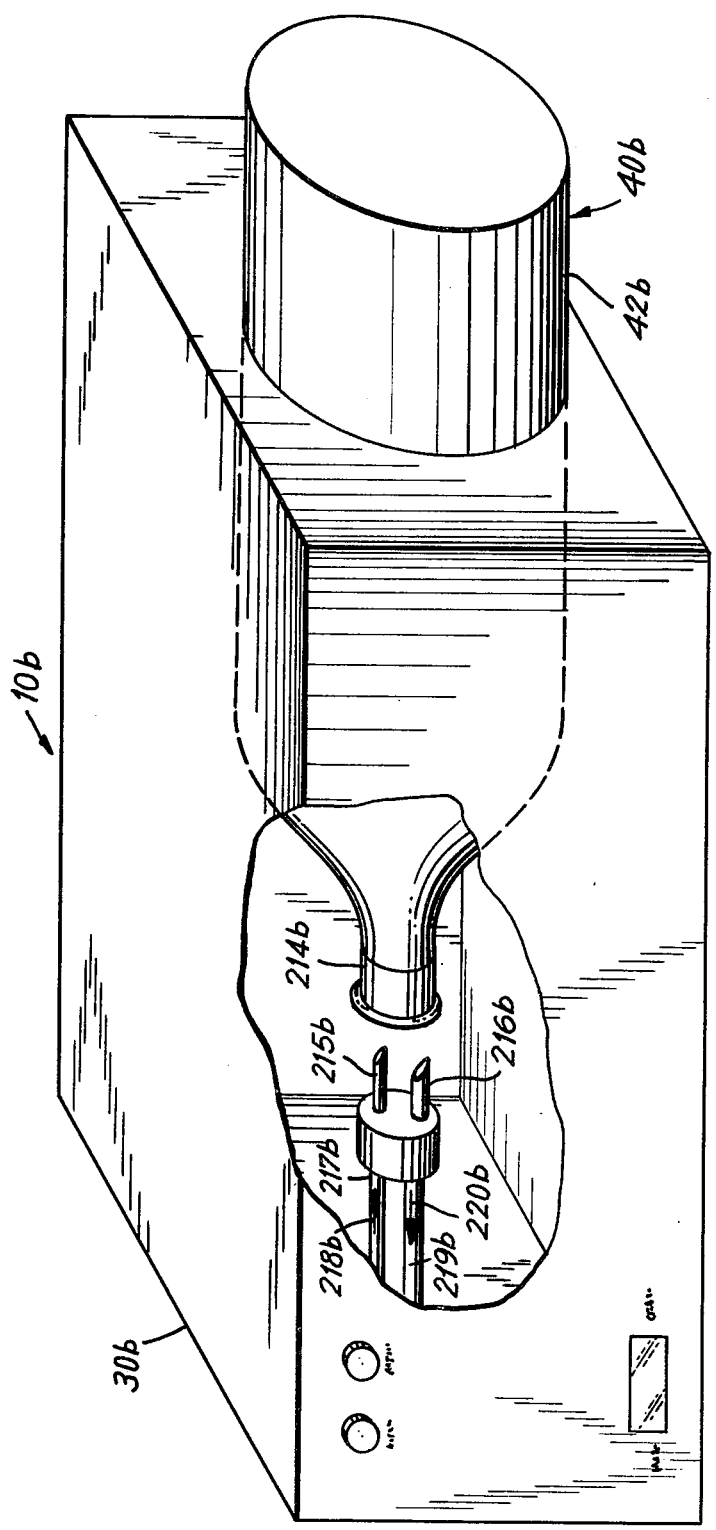

FLUID SUPPLY UNIT FOR DENTAL INSTRUMENTS

CROSS-REFERENCE TO RELATED APPLICATIONS

This application is a continuation-in-part of our co-pending applications Ser. No. 701,536, filed July 6, 1976, and now abandoned and Ser. No. 843,416, filed Oct. 19, 1977, which entire subject matter of the co-pending applications is incorporated herein by reference as if fully set forth herein.

BACKGROUND OF THE INVENTION

The present invention relates to a unit adapted to be used primarily in conjunction with conventional professional dental equipment including ultrasonic prophylaxis and high and low speed drill units and other units to perform a variety of functions or procedures.

Although for illustrative purposes the invention will be described as an adjunct to ultrasonic prophylaxis equipment, it should be understood that the invention can also be used in conjunction with dental drills and other equipment. Heretofore, except for U.S. Pat. No. 3,924,335, the use of ultrasonic energy in dentistry for professional purposes has been limited to the use of water as the fluid utilized within dental prophylaxis procedures in order to remove foreign substances from within the oral cavity and perform other dental procedures. The present inventors have now discovered that it is possible to adapt conventional ultrasonic prophylaxis units as well as dental drills presently in use, and being purchased by the dental profession, to have the capacity to deliver selected fluids to the operative site. Conventional dental units as manufactured by several companies presently use tap water as the fluid to aid in the cooling and/or dental cleaning process. As the drinking water condition deteriorates, and from time to time in certain cities is undrinkable for periods of time, the dentist with his present equipment has no choice but to continue using tap water in his units.

The number of conventional dental ultrasonic prophylaxis units in use today is believed to approximate 100,000 units on a world wide basis. The number of dental drills in use is far greater than that. In addition, annual sales of new ultrasonic prophylaxis units is believed to approximate 20,000 units per year. Many of the new units are purchased by dentists opening their first or a second operatory as well as replacement of older units.

The ability to adapt the units presently in use to pump a fluid selected by the dentist or oral hygienist will permit a savings to the dentist in that only an accessory or auxiliary unit in accordance with this invention need be purchased. Accordingly, by use of the present invention a host of dental procedures not heretofore available may be realized by a system that permits dentists to select fluids having various chemical formulations such that both physical and phychological beneficial results are obtained for their patients. By the provision of the accessory unit of the present invention interchangeable and replaceable fluid supply sources can be directed through the conventional dental handpieces, the scope and variety of dental techniques are increased to a considerble extent. It might be stated that this additional flexibility given to the dentist permits a number of dental procedures to be carried out that were heretofore not practicable with his conventional equipment.

By way of background, the use of Kilohertz ultrasonic energy in the dentist's office has become commonplace. At present all of the professional ultrasonic dental units being marketed do not provide an option to the dentist as to a choice of fluid use. The inventors have now discovered that the benefits set forth in the above referenced U.S. Pat. No. 3,924,335 can be obtained with an auxiliary unit so that presently existing units on the market can be easily adapted to give the user a choice of fluid.

The inventors have been involved in the historical growth of these techniques and procedures, and have carefully followed and evaluated the changing requirements which improved ultrasonic dental equipment should embody. In this patent, such novel improved equipment and new techniques are provided for.

The removal of calculus from gingival and subgingival hard tooth surfaces (dentin and enamel) is one of the chief problems facing the periodontist in treating the undesirable conditions found in the mouth, and is essential for maintaining and restoring good dental health. A chemical solution is often used which selectively stains plaque and calculus and thereby assists the dentist in determining the thoroughness of a given prophylactic oral treatment. Such a solution is called a disclosing solution. A self contained medicament fluid container may contain such a disclosing solution and may be conveniently stored away from the unit until it is desired by the dentist for use. Now, if he has used such a procedure, the internal hydraulic system of the auxiliary unit will have its various tubes and conduits filled with the disclosing solution. If the dentist wishes, for example, to use plain water, or a different medicament solution for his next patient or even for the same patient, he may clean out the internal hydraulic system completely so that it is replaced with clear, clean water. As will be disclosed completely in due course, the present invention provides the means needed to accomplish this purpose.

OBJECTS OF THE INVENTION

An object of the present invention is to provide an auxiliary fluid supply unit that is adapted to be used in conjunction with commercially available professional dental equipment.

Another object of the present invention is to provide a fluid supply unit that can remotely control the electrical operation of a standard dental instrument and simultaneously provide selected fluid medicaments thereto.

Another object of the present invention is to provide a novel fluid supply unit that can be readily installed to operate in conjunction with conventional ultrasonic prophylaxis units.

Other objects and advantages of the invention will be apparent as the disclosure proceeds.

SUMMARY OF THE INVENTION

The present invention includes a fluid supply unit to remotely supply, activate and control the flow of fluid within a conventional dental instrument. The dental instrument includes a power supply, fluid control valve and a handpiece with a tip adapted to be inserted within the oral cavity for simultaneously supplying fluid and energy from the power supply to the handpiece for generally operating the tip and providing fluid adjacent the work site.

The fluid supply unit of the present invention includes fluid coupling means adapted for connecting the fluid supply unit to the dental instrument so that fluid is communicated through the fluid control valve to the dental handpiece. Fluid reservoir means is provided to permit the utilization of a variety of fluids for performing oral hygienic procedures with the dental instrument. Dispensing means if operatively associated with the coupling means and the reservoir means, and is comprised of pumping means communicating with the fluid reservoir means for pumping fluid from the reservoir means through the coupling means to the dental instrument and hydraulic system means.

The hydraulic system means includes first and second valves. The first valve having inlet and outlet ports with the inlet port connected to the pumping means and the outlet port connected to the coupling means. The second valve also has inlet and outlet ports, with the inlet port connected to the pumping means and the outlet port vented to the atmosphere such that the operator may sequentially activate either of the valves to first vent the fluid supply unit and then pump fluid therefrom to the dental instrument.

Control means for electrically connecting the dental instrument to the fluid dispensing means so as to remotely operate the dental instrument and the fluid supply unit is provided. The control means includes first switch means electrically connected to the dental instrument, the first and second valves of the fluid dispensing means are connected to a source of electrical energy. Second switch means is operatively connected to the first switch means such that activation of the second switch means simultaneously remotely activates the dental instrument to obtain power from the power supply to operate the tip extending from the handpiece and open the fluid control valve to permit the flow of the fluid therethrough.

In accordance with one embodiment of the invention, rinsing switch means is operatively associated with the first switch means of the control means to simultaneously activate the dental instrument and the fluid dispensing means to permit a rinsing of the supply unit and the dental instrument.

The dental instrument used on conjunction with the present invention may be in the form of a dental drill with the drill or tool forming the tip thereof. Further, the instrument may include a lavage with the tip at one end thereof. Accordingly, the present invention may be used in conjunction with a dental stand of the fixed or portable design for supplying sterile water thereto.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 13 is a diagrammatic view illustrating an alternate embodiment of the invention in which an air pump is utilized for pumping the fluid; and FIG. 14 is a perspective view illustrating the features of the embodiment illustrated in FIG. 13.

DETAILED DESCRIPTION OF THE DRAWINGS

Figure 1:
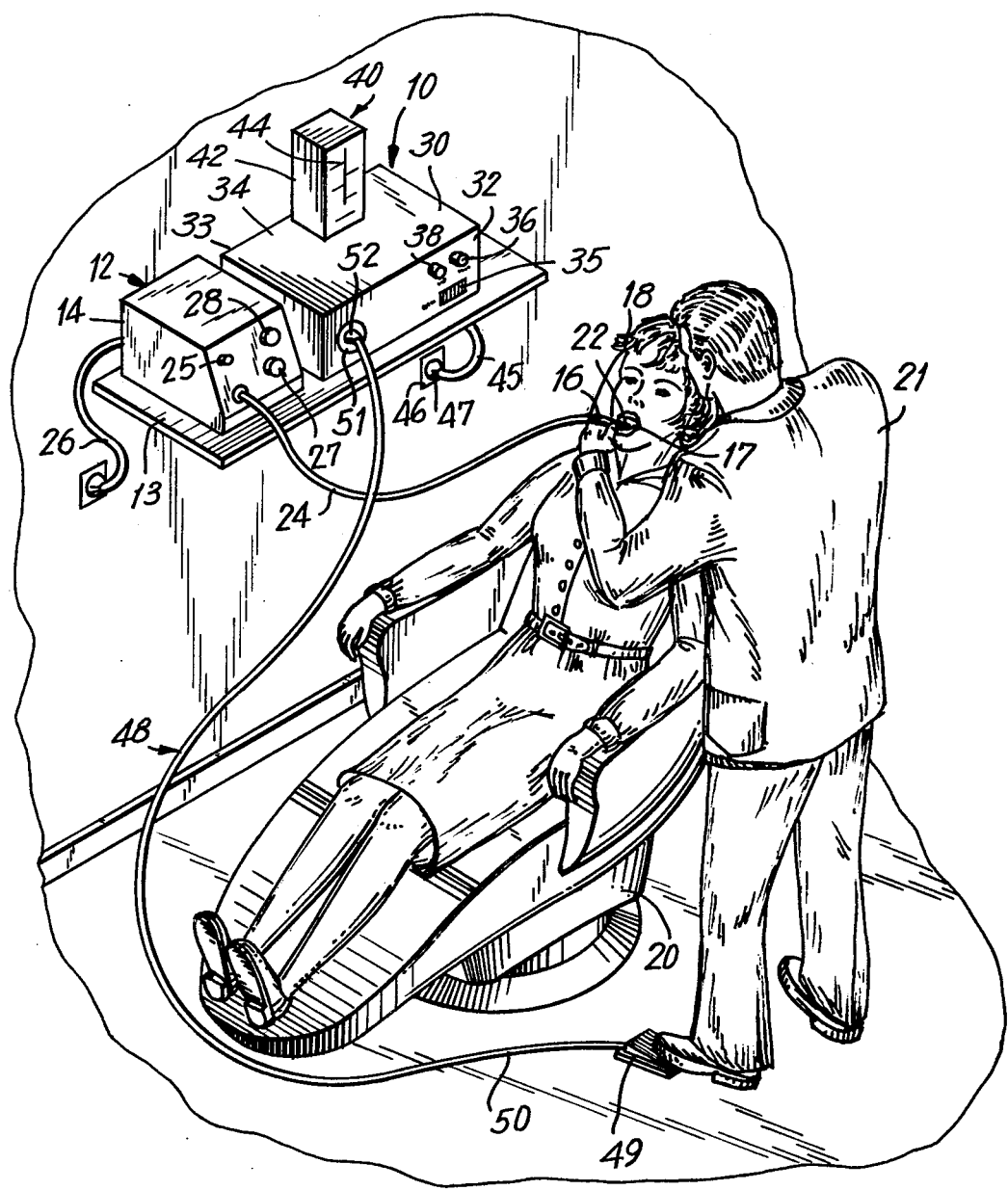
FIG. 1 is a perspective view of the fluid supply unit in operation with a conventional ultrasonic dental prophylaxis unit in accordance with the present invention.

Referring now to the drawings, and initially to FIGS. 1–11, there is illustrated an auxiliary fluid supply unit 10 that is adapted to be used in conjunction with a variety of commercially availble dental or medical instruments or units 12 that are well known and in use today in dental offices around the world. For purposes of illustrating the present invention, the instrument used in conjunction with the fluid supply unit 10 is an ultrasonic prophylaxis unit hereinafter described in greater detail. The fluid supply unit 10 and dental instrument 12, the combination of the two also referred to herein as the ultrasonic fluid supply and dental system, may both be positioned on a table or other support 13 adjacent each other, or spaced from each other up to several feet but functioning in unison. The ultrasonic dental prophylaxis instrument 12 is comprised of a generator 14 that may take various forms and shapes that has a handpiece 16 for use within the oral cavity 17 of a patient 18 that is illustrated in a reclined position on a dental chair 20 being treated by a dentist or other trained person 21. It is appreciated that the construction and function of generator 14 will vary depending upon the instrument 12 with which unit 10 is being used.

The dental instrument 12 includes a tip 22 extending from one end of the handpiece 16 that is inserted within the oral cavity 17 to perform a variety of functions well known in the art. The tip 22 may be in the form of a drill bit or tool for general dental use or as the output end of a lavage device well known in dentistry. The generator 14 is contained in a cabinet 15 and is connected to to the handpiece 16 by means of cable 24 which carries both the fluid supply lines thereto, as well as the power line to supply the electrical energy to the handpiece 16. The handpiece 16 has an ultrasonic motor contained therein for ultrasonically vibrating the tip 22 and providing fluid adjacent the work site on a command basis as requiried by the dentist 21.

The dental instrument 14 normally contains a power ON-OFF switch 25 to permit the line current received through the power line cord 26 to energize the dental instrument 12. In addition, the dental instrument 12 normally includes a fluid regulating valve with a handle or knob 27 that is adjustable to regulate the flow of the amount of fluid through the cable 24 and out of the handpiece 16. A fluid control valve mounted in the generator 14 is connected to the fluid regulating valve, and in the open position thereof water then flows through the handpiece 16. The dental units 12 also include power regulating means having a control knob 28 so that the amplitude of ultrasonic vibration at the tip 22 may be varied. These are the essential features contained in commercially available dental prophylaxis instruments presently on the market.

Prior to the present invention the dentist would normally activate the instrument 12 by means of a footswitch, and the supply of fluid would be ordinary tap water which the inventors believe should be avoided for use in the various dental procedures performed by the dentist. Although the dental instrument 12 has been illustrated to be housed as a separate unit, there are commercially available ultrasonic dental instruments that form part of a console with other non-ultrasonic dental instruments that are presently available and in use in dental offices. The present invention is adapted to be used even with the ultrasonic dental prophylaxis instrument that is contained in a console. In addition, there are those units in which the dentist has a fingertip switch on the handpiece in lieu of a footswitch and the present invention is adaptable for use with there types of instruments as well.

In view of the fact that there is presently in existence tens of thousands of units in dental offices, the fluid supply unit 10 of the present invention was so designed to be compatible for use therewith without the necessity of modifying the existing dental instruments 12 and without having to rework or even enter the generator 14 to make any modifications thereto. This was an important consideration in order to permit quick and easy installation of the auxiliary fluid supply unit 10 in the dental office so that the dentist or even his assistant could place the auxiliary supply unit 10 in operation.

As illustrated in FIG. 1, the fluid supply unit 10 includes housing means 30 which may be in the form of a cabinet having a front panel 32, rear panel 33, and upper surface or wall 34. Certain controls are contained on the front panel 32 and include a power energizing means in the form of a switch 35 having ON and OFF positions, which may include an indicator light therein so that the user is aware when the switch 35 is in its ON position. A fluid prime or venting switch 36 is provided on the front panel 32 and permits the user to first vent the auxiliary fluid supply unit 10 in a manner hereinafter described in detail. A rinse or flushing switch 38 is provided on the front panel in order to permit a manual opening or activation of both the auxiliary fluid supply unit 10 and the dental instrument 12 to obtain a flow of fluid from the reservoir means 40.

The reservoir means 40 is illustrated as mounted on the cover 34 and may take various shapes and forms, as well as being of various sizes. The fluid reservoir means 40 may be in the form of a transparent glass or plastic container or bottle 42 having indicia means 44 thereon which may be in the form of calibrated markings to assist the dentist viewing the amount of fluid therein available. To power the fluid supply unit 10, a power cord 45 is plugged into a conventional wall outlet 46 by means of power plug 47.

The operation of both the supply unit 10 and the dental instrument 12 is controlled by the dentist by the utilization of a footswitch assembly 48 that includes a footswitch 49 that is connected by means of footswitch cable 50 to an electrical outlet 51 on the front panel 32. A male plug 50 is generally contained at one end of the footswitch cable 50 to be plugged into the outlet 51. It is appreciated that the outlet 51 has been shown on the front panel 32 for illustration purposes and may be easily contained or positioned on the rear panel 33 of the supply unit 10.

The cable assembly 48 may vary as to the particular plug 52 that is used on different model ultrasonic dental units of different manufacturers and accordingly either a plug adapter is utilized or perferably the fluid supply unit 10 may come in various models with each model adapted to be used with a different manufacturer or a different manufacturer's model. This flexibility also permits the dentist to utilize the footswitch available with the dental instrument 12 that he presently has in his office.

Figure 2:
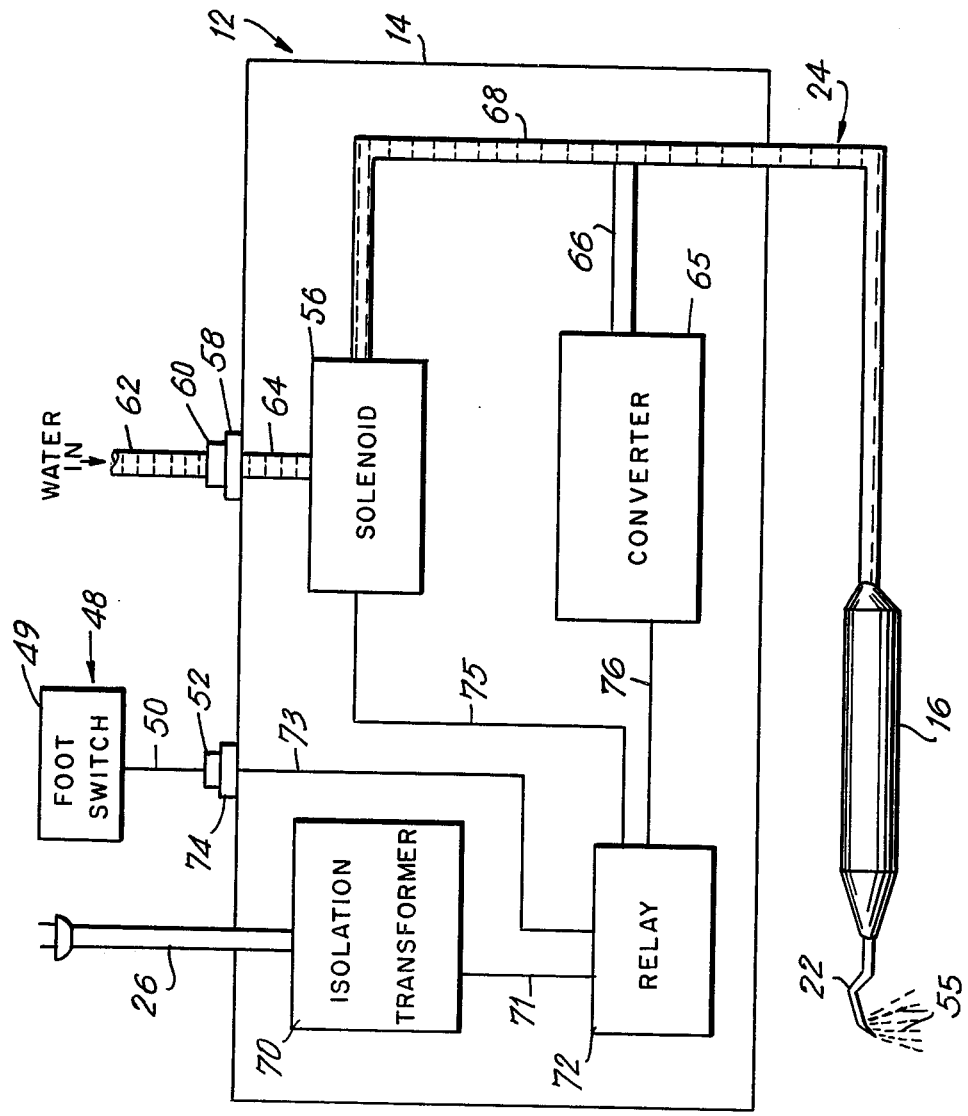
FIG. 2 is a diagrammatic in view illustrating the various components of a standard dental instrument.

Referring now to FIGS. 2-11, the diagrammatic and electromechanical operations of the fluid supply unit 10 and dental instrument 12 and the interrelated operational features therebetween are described with respect to these figures. Referring now to FIG. 2, there is illustrated the normal functional relationship of the standard dental unit 12, which includes the handpiece 16 with the tip 22 extending from one end thereof and with fluid 55 exiting at or adjacent the tip 22. A variety of either flow-through tips 22 are available, or those in which a fluid outlet tube terminates adjacent the tip 22 are also commercially available, and the equipment of the present invention is adapted for use with both these types as well as with magnetostrictive or piezoelectric motors contained within the handpiece 16.

The generator 14 normally has contained therein a water solenoid or fluid control valve 56 to which fluid enters through a fluid coupling adapter 58 that is mounted on the rear wall of the generator cabinet 15. The adapter 58 generally receives and mates with a coupling adapter 60 contained at one end of the fluid conduit or tubing 62. The other end of the conduit 62 normally has an associated coupling member that is connected to the conventional source of water. Within the generator 14 there is an appropriate conduit 64 connecting the fluid adapter 58 to the solenoid 56. The cable assembly 24 is adapted to transmit both the fluid 55 and electrical energy from the converter 65 forming part of the generator 14. An electrical lead 66, shown schematically, is joined to the fluid conduit 68 extending between the solenoid 56 and the handpiece 16.

The power cable 26 is connected to an isolation transformer 70, which in turn is connected electrically by lead 71 to a switch in the form of a relay 72, which in turn is connected by footswitch lead 73 to a receptacle connector or plug 74 mounted on the exterior of the generator 14. The footswitch assembly 48 has the power cord 50 running from the footswitch 49 with the plug 52 adapted to mate with the connector 74. The relay 72 is electrically connected by lead 75 to the solenoid 56, and the relay 72 is also electrically connected by lead 76 to the converter 65.

Under normal operating conditions activation of the footswitch 49 closes the circuit through the relay 72, and the solenoid 56 is brought into an open position permitting fluid from the outside source through conduit 62 to flow therethrough, and simultaneously the converter 65 is activated in order to ultrasonically vibrate the tip 22. The manual fluid control knob 27 on the generator cabinet 15 is coupled to the solenoid 56 in a manner not shown to regulate the volume of fluid 55 flowing through the unit.

Figure 3:
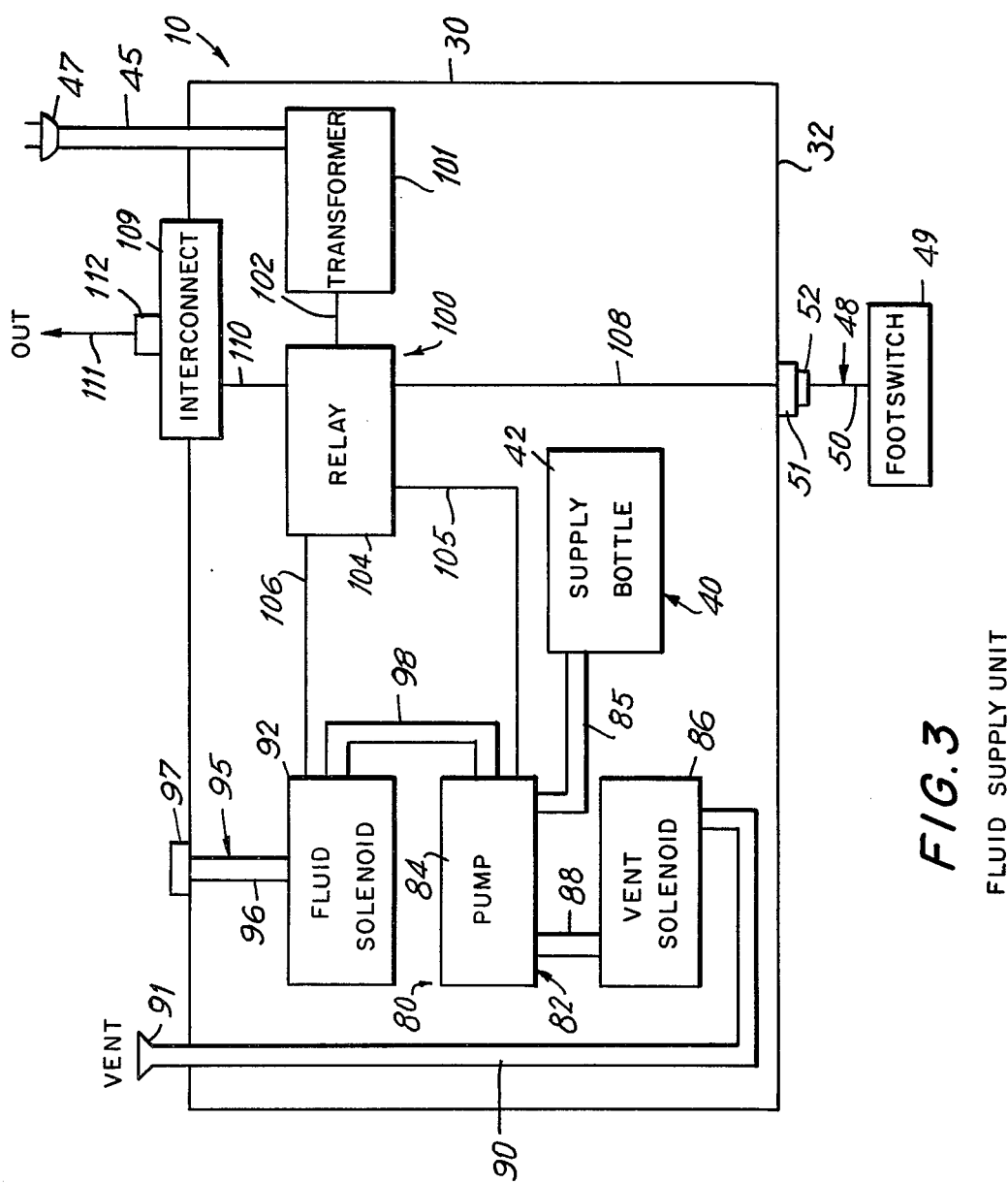
FIG. 3 is a diagrammatic view illustrating the various components of the fluid supply unit in accordance with the present invention.

Referring now to FIG. 3, the auxiliary fluid supply unit 10 is diagrammatically illustrated prior to its connection with the dental instrument 12. The housing means 30 has either mounted therein or associated therewith various hydraulic and electrical components adapted to operate on an interrelated basis with each other and in conjunction with the dental instrument 12 in order to remotely power same as previously discussed. As seen in FIG. 3, the block diagram illustration indicates that the footswitch assembly 48, including footswitch 49 having cable 50 extending therefrom, is joined to the receptacle 52 which is electrically connected to the connector 51, which may be mounted on the front panel 32.

Operatively associated with the fluid reservoir means 40 is fluid dispensing means 80 which may include in interconnected fashion pumping means 82, which includes a pump 84 that may take various forms and shapes. The pumping means 82 is connected with the fluid reservoir means 40 by reservoir interconnecting means 85 to permit a continuous flow to be available to the pump 84 from the fluid reservoir container 42.

In those instances where the pump 84 has been left to run dry, it has been found necessary to effectively prime the pump to eliminate any trapped gas, generally air, that is contained therein such that the fluid in the container 42 may flow out. To accomplish this, the user will engage the venting switch 36 on the front panel, thereby opening the venting means in the form of a second valve or vent solenoid 86 which is connected to the pump 84 by venting interconnecting means 88, and the opposite end of the venting valve 86 is connected to the atmosphere by venting conduit 90 terminating in an open end 91.

To control the flow of fluid out of the fluid supply unit 10, a first valve or fluid control solenoid 92 is provided that has one end thereof connected to fluid coupling means 95 adapted for connecting the fluid dispensing means 80 to the ultrasonic dental instrument 12 so that fluid from the fluid dispensing means 80 is communicated to the dental handpiece 16. The fluid from the pump 84 is transmitted through pump interconnecting means 98 that joins together the pump 84 and fluid solenoid 92. The fluid coupling 95 may include a coupling conduit 96 that terminates in a supply unit coupling member 97. The coupling member 97 is in turn adapted to be coupled to the fluid coupling member 58 provided with the generator 14.

Remote control means 100 is provided for electrically connecting the ultrasonic dental instrument 12 to the fluid dispensing means 80 for simultaneously energizing the ultrasonic dental instrument 12 and the auxiliary fluid supply unit 10. The control means 100 has the power cable 45 receiving electrical energy from the connection of the wall plug 47 to the power outlet 46 and connected to a step down transformer 101 that is connected by electric transformer coupling means 102 to a first switch means or relay means 104. The first switch means 104 is electrically connected by electric lead mean 105 to the pump 84 and by fluid electric lead means 106 to the fluid solenoid 92. Footswitch lead means 108 interconnects connector 51 to the first switch 104, and an interconnect connector 109 is connected by interconnecting means 110 to the first switch 104.

Associated with the interconnect connector 109 is an interconnect power cable 111, which may be adapted to have a removable connector 112 associated therewith in order to make the electrical interconnect cable 111 readily removable from the auxiliary fluid supply unit 10 as well as the dental instrument 12. Although separate fluid cables and electrical cables interconnect the dental instrument 12 and the fluid supply unit 10, they my be incorporated in one cable if the conventional ultrasonic dental instrument permits.

FIGS. 4, 6, 8 and 10 are diagrammatic in nature and are provided to illustrate by pictorial representations that the supply unit 10 can remotely operate the hydraulic and electrical systems associated therewith to permit the operator to carry out the necessary functions of the dental instrument 12 from a remote unit in accordance with the present invention. Accordingly, these figures are provided to more fully describe the electrical and hydraulic aspects of the present invention, and the combination pictorial representations and schematic circuit diagrams illustrate the operational aspects of the hydraulic and electrical systems.

FIGS. 5, 7, 9 and 11 are combination pictorial representations and schematic circuit diagrams which illustrate the operational aspects of the electrical and hydraulic systems so as to permit the remote control of the dental instrument 12 and simultaneous operation of the fluid supply unit 10.

Figure 4:
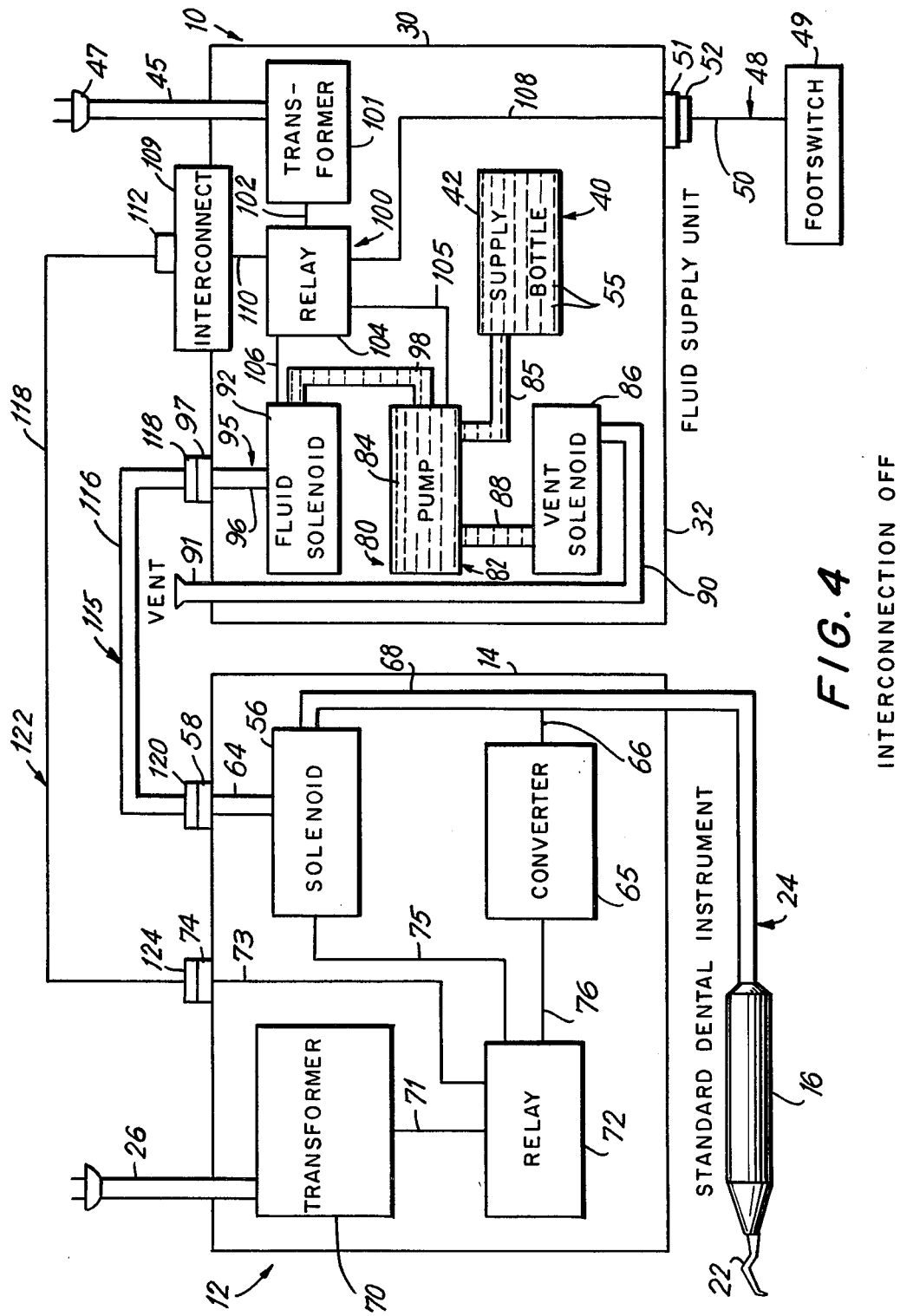
FIG. 4 is a diagrammatic view illustrating the interconnection of the combined standard dental instrument and fluid supply unit, electrically and hydraulically coupled together in the "OFF" condition thereof.
Figure 5:
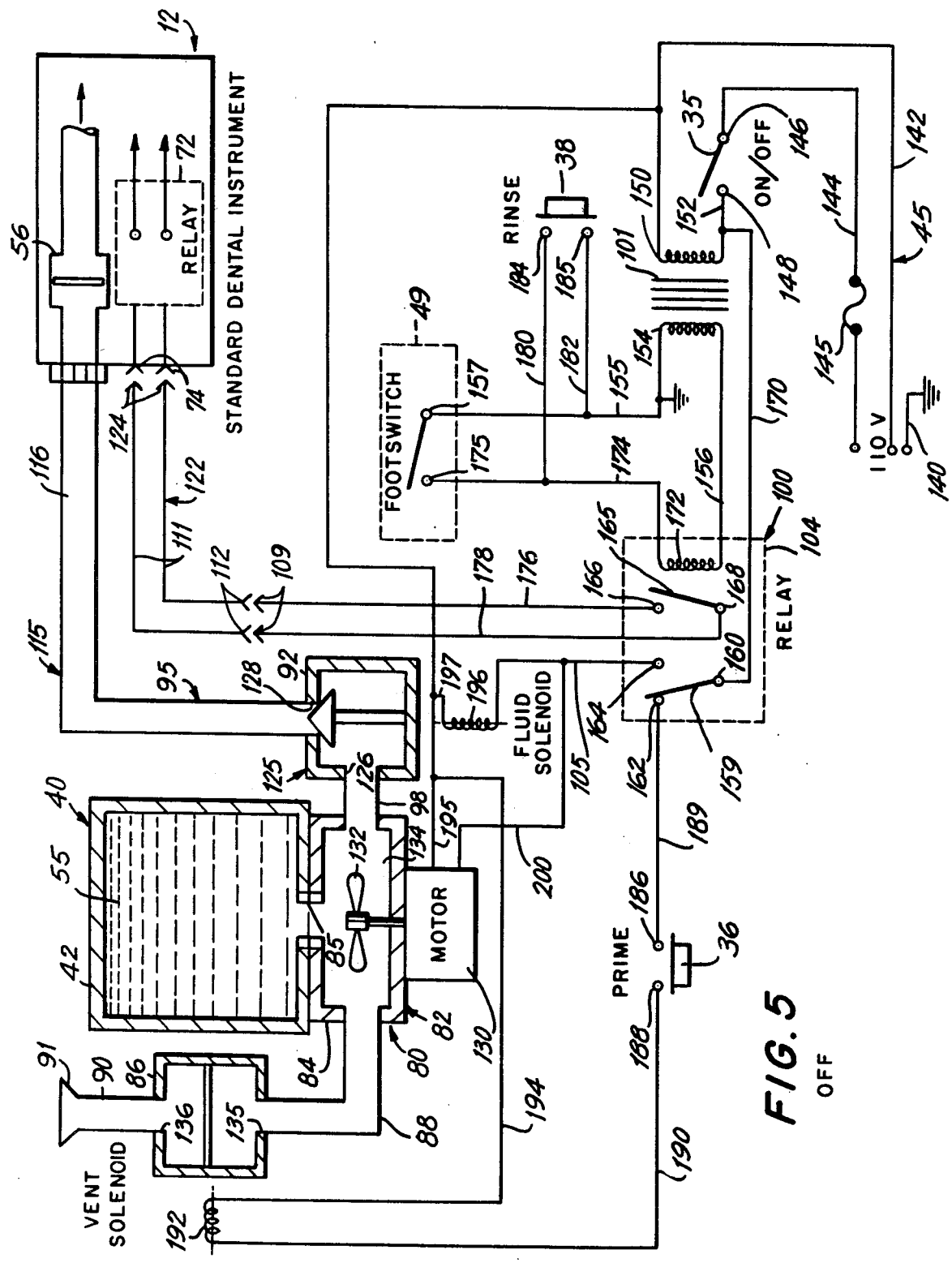
FIG. 5 is a schematic more or less diagrammatic view of the combined standard dental instrument and fluid supply unit illustrated in the "OFF" position of FIG. 4.
Figure 6:
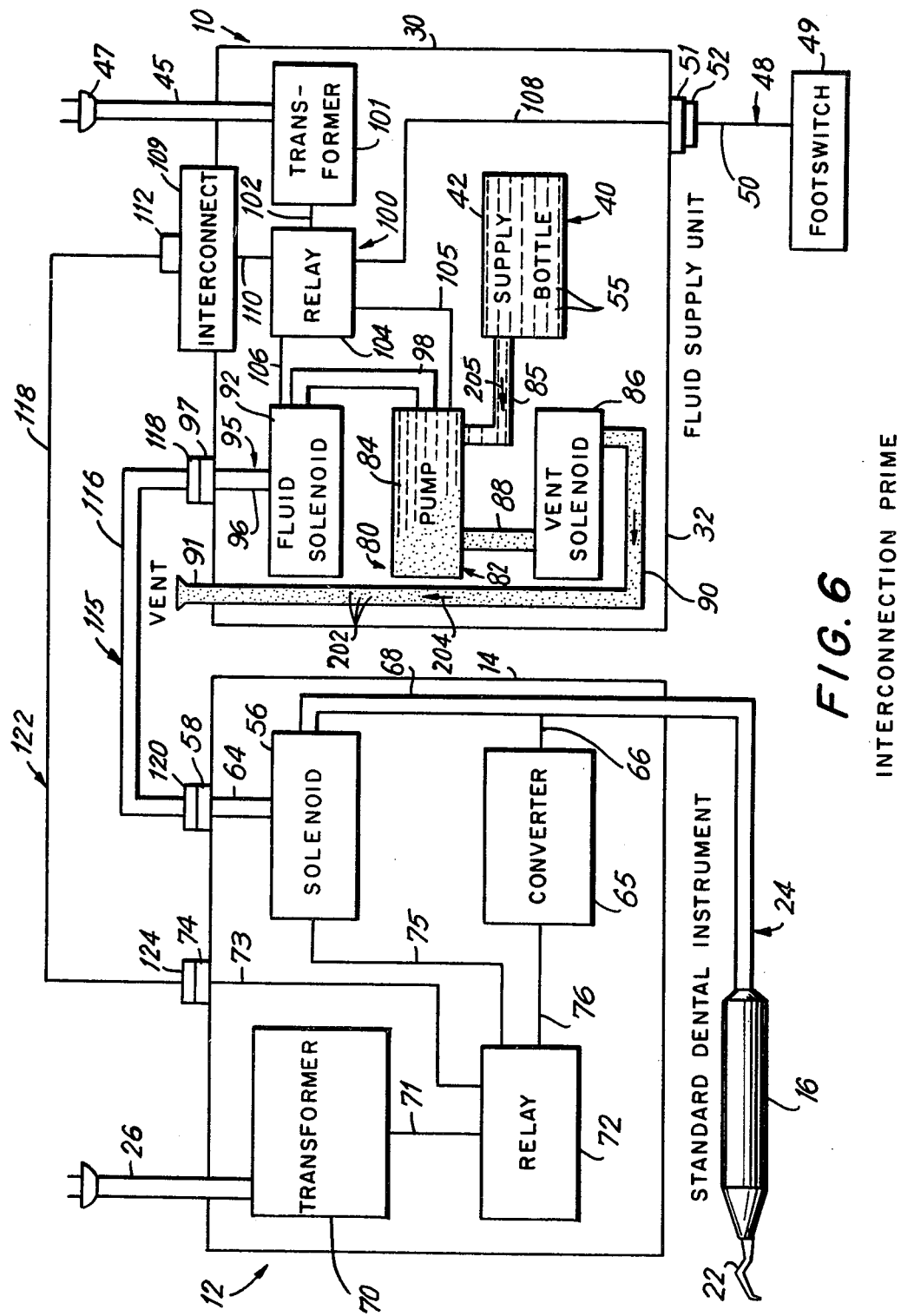
FIG. 6 is a view similar to FIG. 4 illustrating the "PRIME" interconnection.
Figure 7:
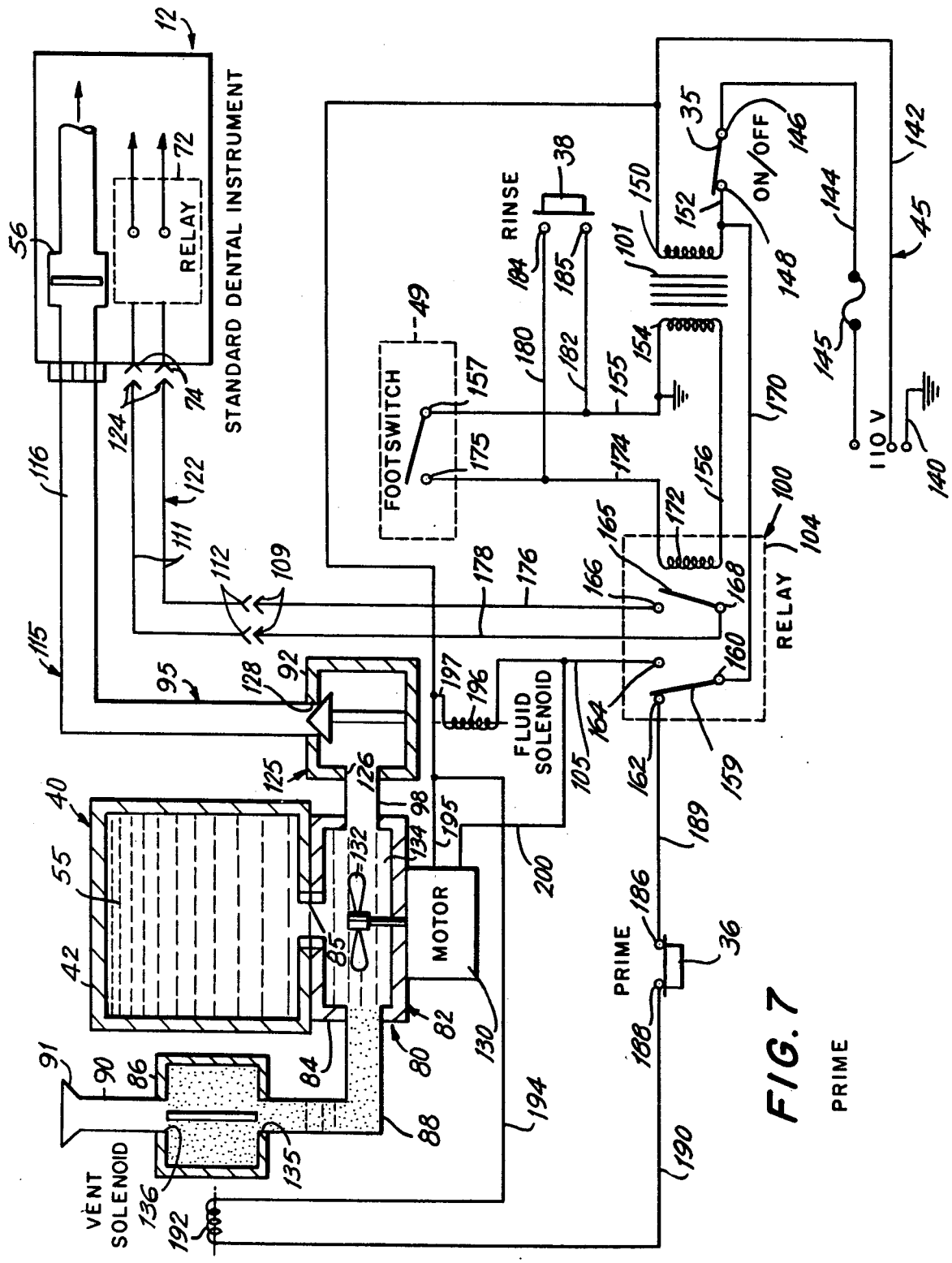
FIG. 7 is a view similar to FIG. 5 but illustrating the "PRIME" interconnection set forth in FIG. 6.
Figure 8:
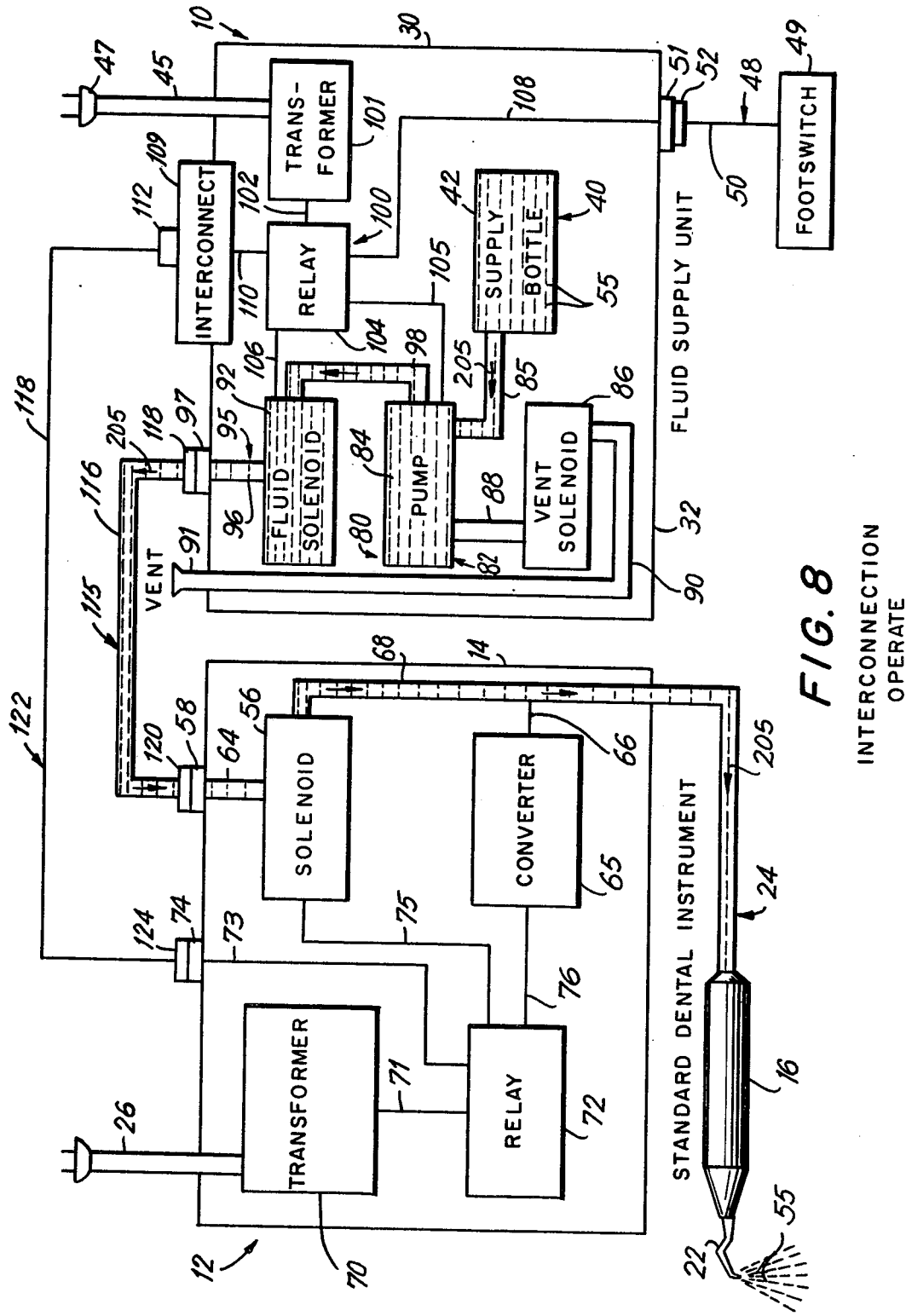
FIG. 8 is a view similar to FIG. 4 illustrating the "OPERATE" interconnection.
Figure 9:
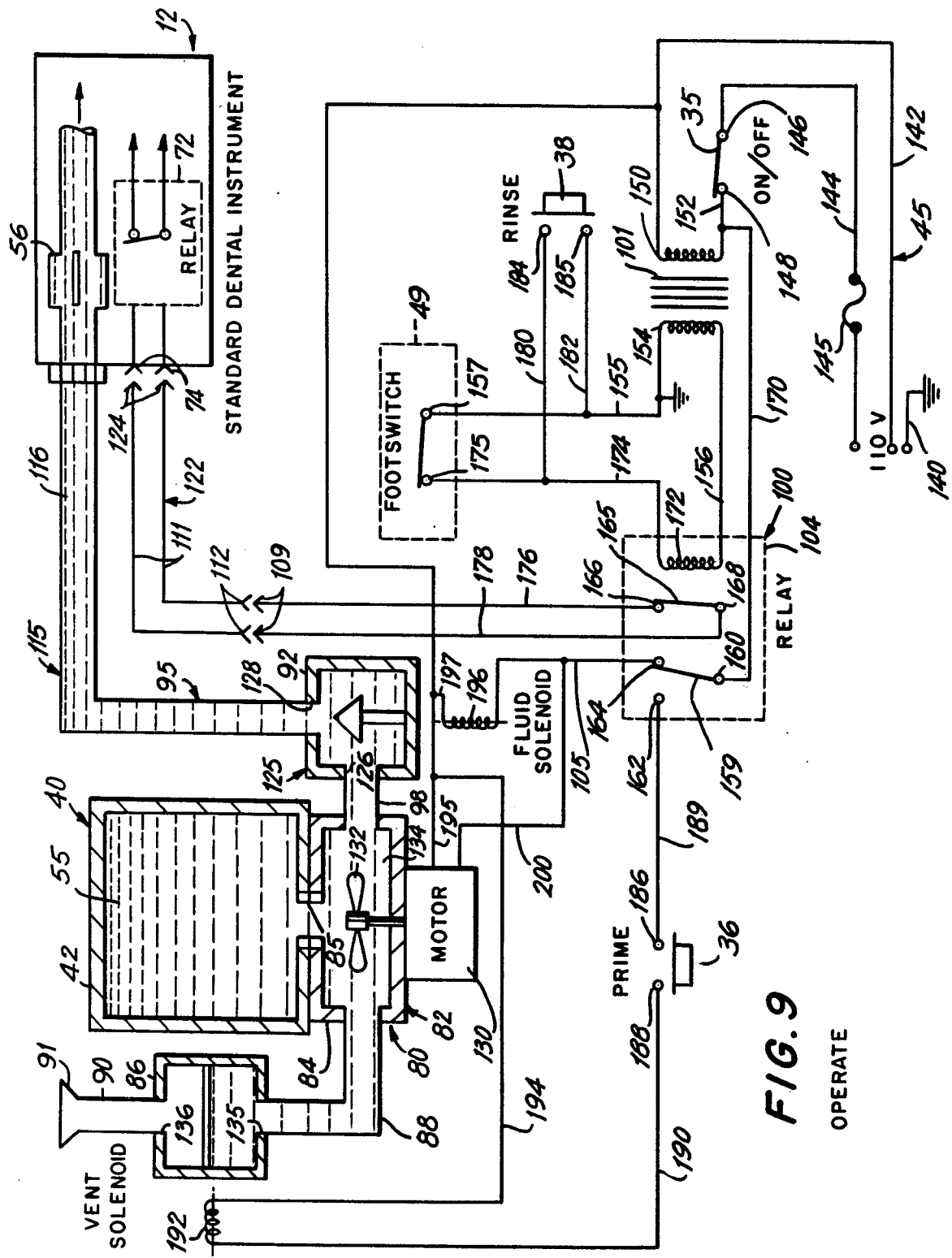
FIG. 9 is a view similar to FIG. 5 but illustrating the "OPERATE" interconnection set forth in FIG. 8.
Figure 10:
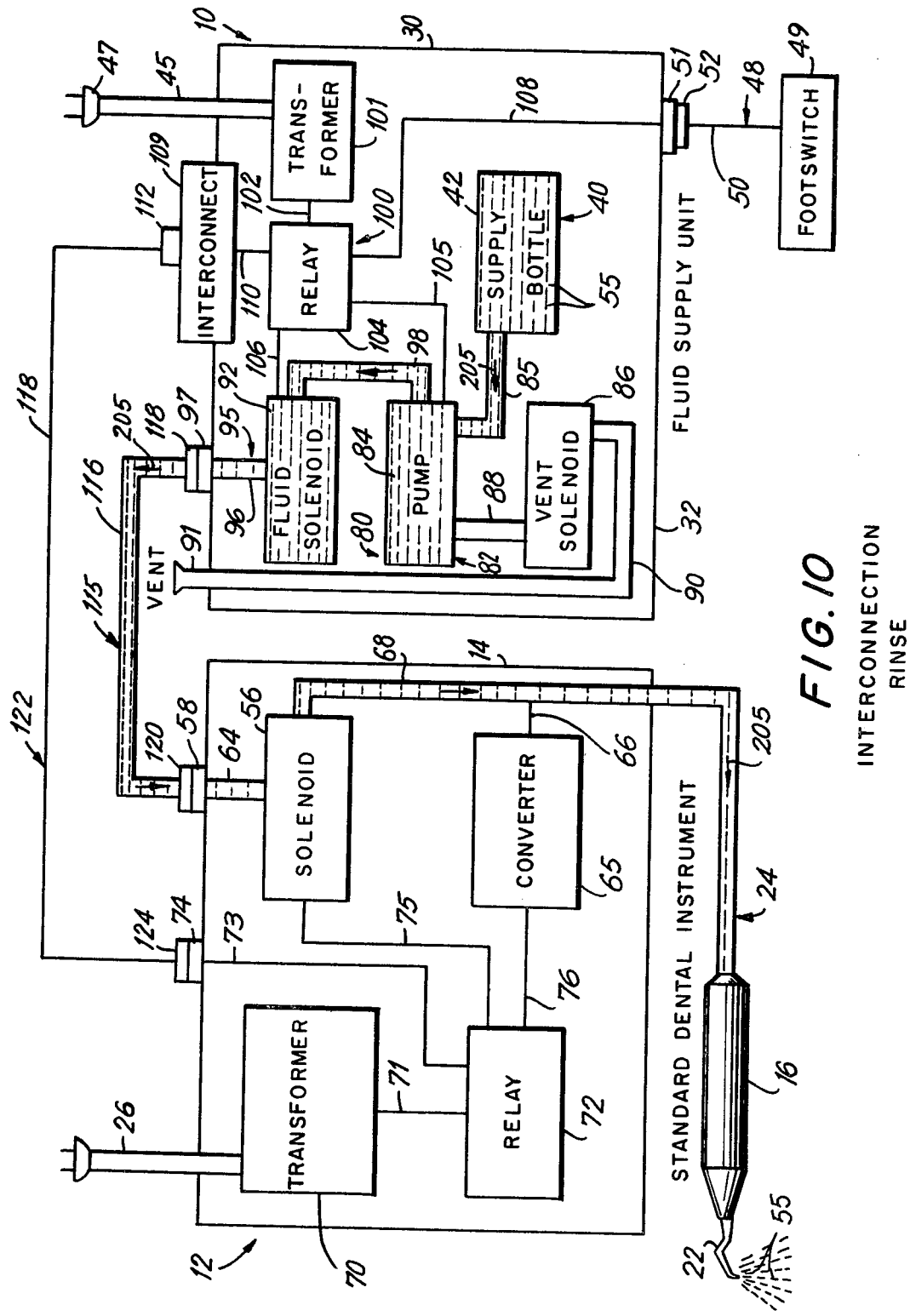
FIG. 10 is a view similar to FIG. 4 illustrating the "RINSE" interconnection.
Figure 11:
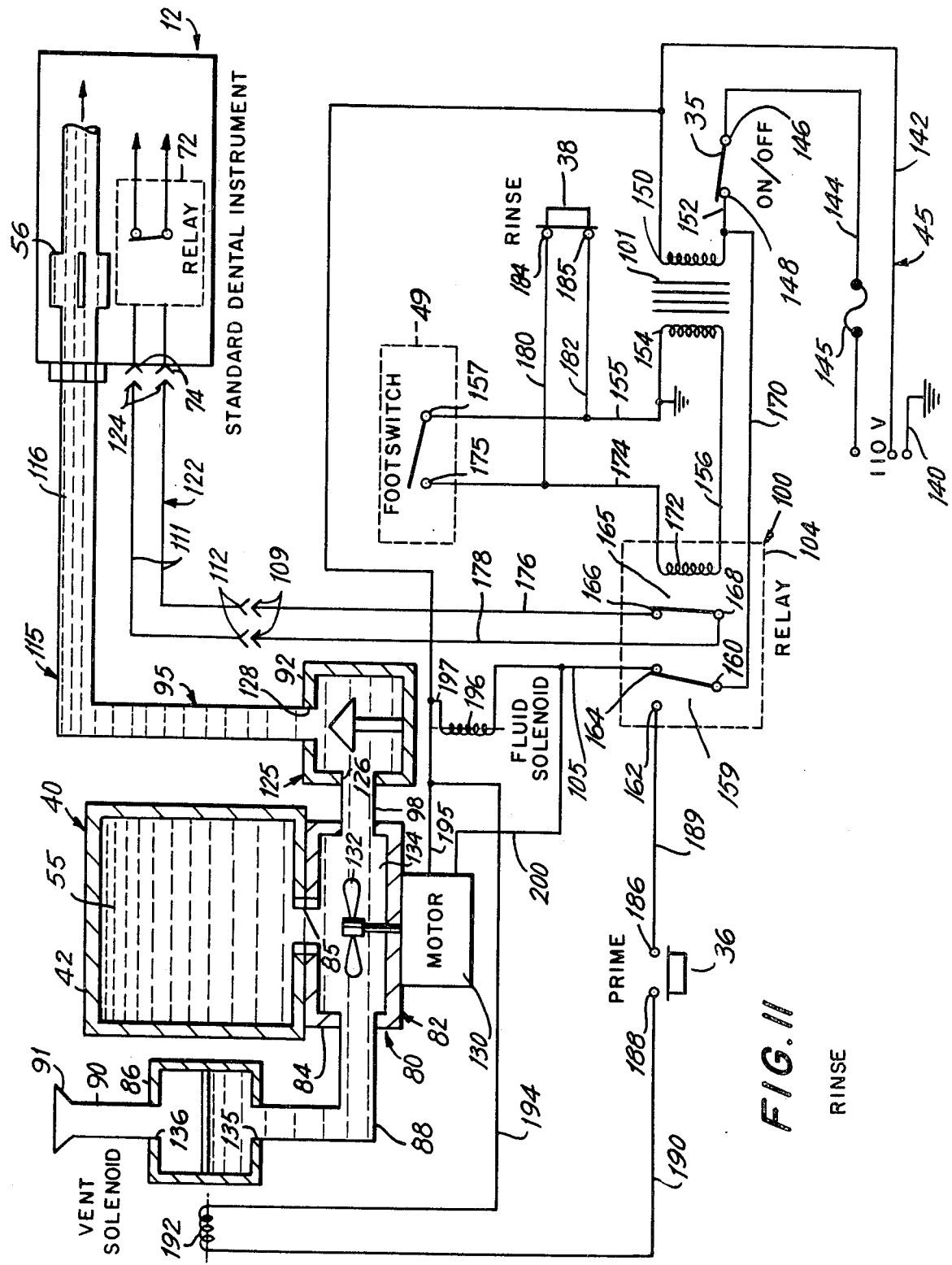
FIG. 11 is a view similar to FIG. 5 but illustrating the "RINSE" interconnection set forth in FIG. 10.

Accordingly, FIGS. 4 and 5 illustrate the supply unit 10 and dental instrument 12 in the OFF position. FIGS. 6 and 7 illustrate the initial step when the pump 84 has run dry and it is desired to initially prime the supply unit 10. FIGS. 8 and 9 illustrate the ultrasonic fluid supply and dental system in the fully operational position. FIGS. 10 and 11 illustrate supply unit 10 and dental instrument 12 when it is desired to rinse the ultrasonic fluid supply and dental system of a particular medicament prior to the introduction of another medicament within the supply unit 10 and dental instrument 12.

FIG. 4 illustrates the interconnection between the supply unit 10 and dental instrument 12 in the OFF condition, in which the standard dental unit 12 previously discussed with respect to FIG. 2 is now connected to the auxiliary fluid supply unit 10 previously discussed with respect to FIG. 3. The interconnect between the two is accomplished in a very simple manner without having to open or in any way modify the dental instrument 12. To accomplish this fluid interconnection, there is provided the fluid coupling means 95 that has the fluid coupling member 97 mounted on the exterior, generally on the rear panel 33, of supply unit 10. The fluid coupling means 95 is adapted to be joined in fluid tight relationship to interconnecting fluid means 115 having a fluid hose cable 116 with a fluid connector 118 at one end and fluid connector 120 at the opposite end. The fluid connector 118 is connected in operative relationship to the fluid connector 97, and the fluid connector 120 is connected in operative relationship to the fluid connector 58.

Although for purposes of illustration the fluid cable 116 has been illustrated, if desired the existing water hose, as illustrated in FIG. 2, consisting of conduit 62 and connector 60, may in fact be utilized after it is disconnected from the tap water supply. This permits a coupling relationship for the fluid between supply unit 10 and dental instrument 12.

The electrical interconnection is accomplished by removal of the footswitch assembly 48 from the electrical connector 74, as illustrated in FIG. 2. The footswitch assembly 48 is now connected by means of plug 52 to the appropriate receptacle 51 mounted on the housing means 30 for activation of the ultrasonic fluid supply dental system. Electrical interconnecting means 122 is provided and is connected between the interconnect connector 108 and the electrical connector 74 that was previously utilized for the footswitch assembly 48. The electrical cable 111 forming part of the electrical interconnecting means 122 has the connector 112 at one end thereof and electrical connector 124 at the other end thereof connected to connector 74. In this relationship the supply container 42 may have the fluid 55 contained therein with a certain amount of fluid within the pump 84 and the ultrasonic fluid supply and dental system is ready for operation.

FIG. 5 illustrates the schematic representation of the ultrasonic fluid supply and dental system in the OFF condition, with hydraulic system means 125 provided to operate in conjunction with the fluid reservoir means 40 and the pumping means 82. The hydraulic system means 125 forms part of the fluid dispensing means 80 and is seen to include a first valve or solenoid 92 having an inlet port 126 and an outlet port 128. The fluid control valve 92 is a solenoid with the outlet port 128 in turn joined to the coupling conduit that forms part of the fluid coupling means 95. The inlet port 126 is joined by the pump interconnecting means 98 to the pump 82 which may include an externally mounted pump motor 130 havng an impeller blade 132 extending within the fluid chamber 134.

The reservoir interconnecting means 85 connects the fluid container 42 to the pump 84 of which the motor 130 forms a part thereof. The fluid container 45 may be of an open or closed type, which contains fluid 55 as explained earlier. The second valve 86, which forms the means for venting the fluid unit 10, similarly has an inlet port 135 that is connected to the pumping means 82 by the venting interconnecting means 88. The second valve or vent solenoid 86 includes an outlet port 136 that communicates with the venting conduit 90 having a free end 91 that generally extends exteriorly of the housing means 30. In this manner a few drops of fluid 55 will exit from the open end 91, and the user will know that the pump 84 has been vented and that there is fluid throughout the hydraulic system means 125.

The electrical wiring is such that the electrical power is supplied from a conventional 110 volt or other source of electrical energy that is brought into the unit by the power cord 45 that would include ground lead 140 and power leads 142 and 144. A power fuse 145 may be provided along power lead 144. The power switch 35 has terminals 146 and 148, and is interposed in the circuit in order to provide electrical current with the closing of the switch 35. The transformer 101 is wired such that when the switch 35 is closed, it permits electric current to enter the primary winding 150 of the transformer 101. Electric lead 152 connects the primary winding 150 to the terminal 148. The step down transformer 101 at the instant the power switch 35 is closed will not change the position of any component in the supply unit 10. By having 110 volts available on the primary side 150 of the transformer 101, the unit is then functional for operational use.

The secondary coil 154 of the transformer 101 has electrical leads 155 and 156 connected thereto. Lead 155 is in turn connected to terminal 157 of the footswitch 49, and lead 156 is wired to the first switch means or relay 104 which forms part of the remote control means 100. The first switch means 104 is seen to include in effect two sets of switches, one being single pole, double throw, and the other being a single pole, single throw. Accordingly, the relay 100 has normally open contact circuit means and a single pole two position circuit means. The first switch means 104 includes a two position circuit means having a contact arm 159 electrically connected to terminal point 160 at one end thereof, and extending for movement between terminals 162 and 164. The single contact means includes a contact arm 165 adapted to engage terminal 166 that pivots about terminal 168. Lead 170 connects the terminal 160 to the lead 152 between the terminal 148 and the primary winding 150.

The relay 104 includes a coil 172, connected via wire 156 to the secondary winding 154, and the other side of the coil 172 is connected, via lead 174, to the other terminal 175 of the footswitch 49. The leads 155 and 174 form the footswitch lead means 108 illustrated in FIG. 4. The terminal 166 is connected, via wire 176, and the terminal 168 is connected, via wire 178, to the interconnect connector 109, which is in turn electrically connected to the removable connector 112 having the interconnect power cable 111 extending therefrom with the electrical connector 124 on the opposite end thereof and forming part of the electrical interconnecting means 122. The electrical connector 124 is in turn connected to the connector 74 to provide electrical energy to the standard dental instrument 12 illustrated diagrammatically in FIG. 5.

Wired across leads 155 and 174 is the rinse or flushing switch 38 illustrated in FIG. 1 and having leads 180 and 182 extending from electrical contacts 184 and 185. Lead 180 is in turn connected to lead 174 and lead 182 is in turn connected to lead 155. Electrically coupled to the terminal 162 of the first switch means 104 is the prime or venting switch 36 illustrated in FIG. 1. The venting switch 35 includes terminals 186 and 188. Terminal 186 is connected via wire 189 to terminal 162, and wire 190 is connected to terminal 188, and to one end of the vent solenoid coil 192. The opposite end of the vent solenoid coil 192 is connected via wire 194 to the lead 195 extending from the motor 130 which lead 195 is connected to the power cable lead 142.

The fluid control valve 92 has a solenoid winding 196 associated therewith with one end connected, via wire 197, to lead 195, and the opposite end connected by electric lead means 105 to the terminal 164. The other lead 200 of motor 130 is similarly connected to terminal 164 by means of lead means 105 and the coil 196. The circuit diagram shown in the OFF condition depicts the basic wiring of the fluid supply unit 10. The rinse or flushing switch 38, prime or venting switch 36, and footswitch 49 are normally open switches, while the fluid control solenoid 92 and venting solenoid 86 are both normally closed valves. The relay 104 contains two sets of switches as explained above. These six components wired in the fashion illustrated in FIG. 5 provide the logic arrangement necessary to supply fluid 55 and control the standard dental instrument 12.

FIGS. 6 and 7 illustrate the interconnection of the ultrasonic fluid supply and dental system in the mode of operation wherein the prime switch 36 has been closed.

As seen in FIG. 6, the purpose of this is to vent the supply unit 10 such that any entrapped air 202 is permitted to escape in the direction of arrow 204 through the vent solenoid 86 and out the venting end 91. By depressing the prime switch 36, 110 voltage current is allowed to pass through the normally closed contacts 160 and 162 of the relay 104 and through the prime switch 36 into the coil 192 of the vent solenoid 86 thereby opening the valve as illustrated in FIG. 7.

As illustrated in FIG. 6, fluid from the supply container 40 enters into the pump 84 and allowed to replace the trapped air 202 in the pump cavity 134. Hence, priming of the pump 84 is accomplished by retaining the venting switch 36 in a closed position. The current needed to activate the vent solenoid 86 is passed through the normally closed set of contacts 160 and 162 in the relay 104. If these contacts 160 and 162 are in a normally open position due to the use of the footswitch 49 or rinse switch 38, priming the pump 84 will not be accomplished. This logic or safety feature is provided to avoid the pumping of fluid out through the vent tube 90.

FIGS. 8 and 9 illustrate the operational mode of the ultrasonic fluid supply and dental system in operation with the fluid 55 now flowing in the direction of arrow 205 and through the cable 24 and the handpiece 16 and out through the tip 22. When stepping upon the footswitch 49 after the system has been primed in accordance with FIGS. 6 and 7, if required, the footswitch 49 making contact between the terminals 157 and 175 will initiate a flow of fluid 55 from the reservoir means 40. The footswitch 49 activates both the ultrasonic hydraulic system 125 by opening the fluid control valve 56 in the dental instrument 12. This is accomplished in the following manner. The closed contacts 156 and 175 in the footswitch 49 completes the circuit between the relay 104 and the 12 volt, or other voltage, supplied by the transformer 101 through leads 155 and 156. This energizes the relay coil 172 and moves the contacts in the relay 104 and as illustrated in FIG. 9, contact arm 165 now extends between terminals 166 and 168.

In addition, contacts 160 and 164 are closed by the contact arm 159, thereby providing 110 volts to the pump motor 130 and fluid solenoid valve 92. At this time the pump 84 is started with the motor 130 turning the impeller 132 and the fluid 55 within the chamber 134 is allowed to pass the open fluid solenoid 92. As seen in FIG. 9, the coil 196 of the fluid solenoid 92, when energized, opens the valve for the fluid 55 to pass.

Simultaneously, as the second set of contacts 166 and 168 are closed by the contact arm 165, the control relay 72 in the standard dental instrument 12 is caused to change position and thereby open the incoming fluid solenoid 56 and simultaneously apply ultrasonic power to the handpiece 16. The second set of contacts 166 and 168 are in effect replacing the contacts of the footswitch 49 when the dental instrument 12 is set up in standard fashion. As discussed above, in the manner described supply unit 10 is capable of remotely controlling the dental instrument 12 so as to obtain a combination of the two units.

FIGS. 10 and 11 illustrate the rinse mode of operation where the dentist desires to flush the ultrasonic fluid supply unit and dental system free of any fluids which may have a tendency to clog the system. The rinse switch 38 is normally in an open position and wired in parallel to the footswitch 49. The electromechanical sequence is the same as the operate mode illustrated in FIGS. 8 and 9 except that it may be desirous of replacing the footswitch 49 with a manually controlled rinse switch 38. This allows the dentist to permit the ultrasonic fluid supply and dental system to flush itself without the need to physically hold down the rinse switch 38. Therefore, although the rinse switch 38 has been illustrated of the holddown type, a toggle switch could be used so that fluid to flush out the system has more than sufficient time to complete the rinsing stage. Accordingly, the sequence of operation for rinsing is illustrated in FIGS. 10 and 11.

Figure 12:
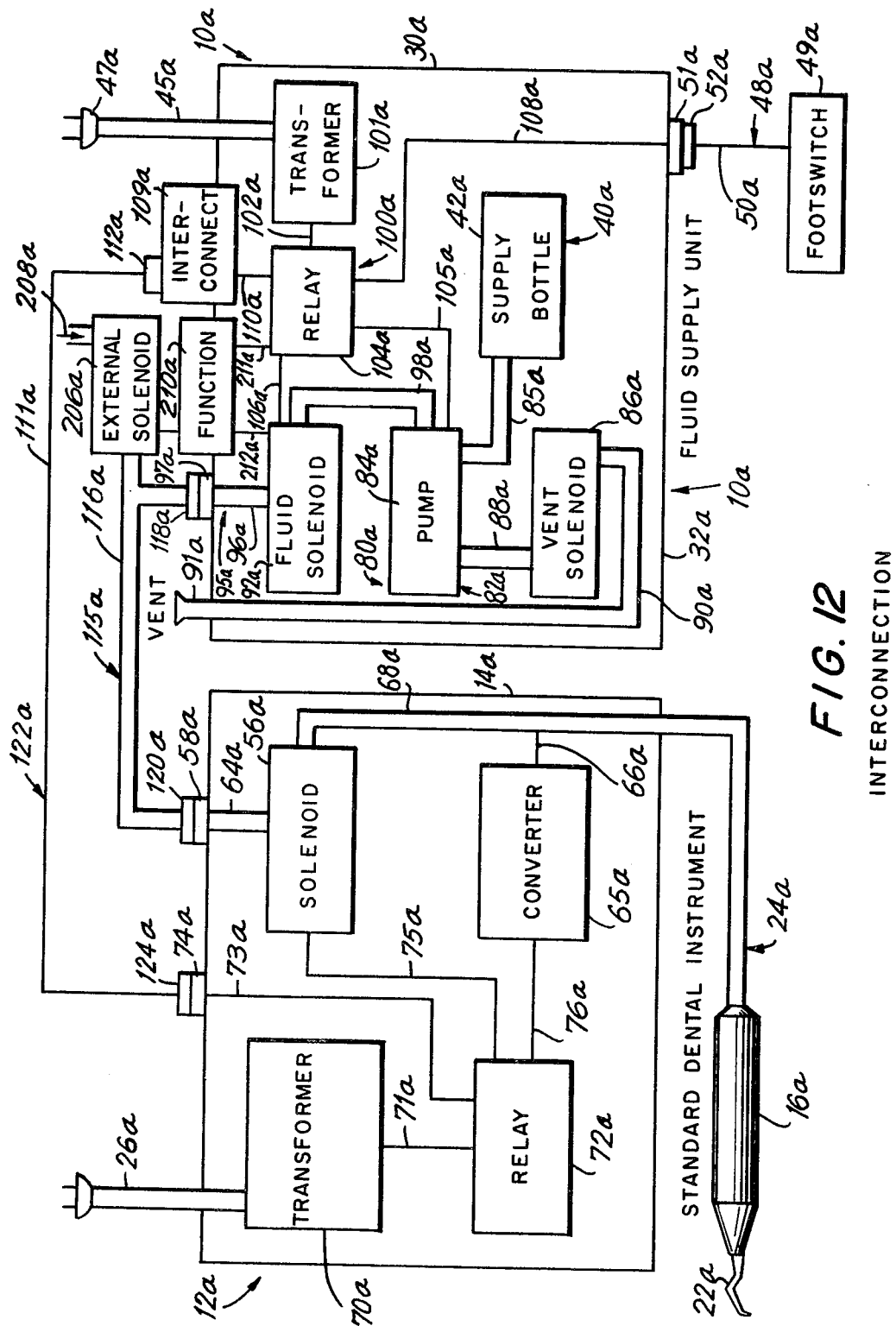
FIG. 12 is a view similar to FIG. 4 but illustrating an alternate embodiment of the present invention in which fluid may be supplied from an external source.

FIG. 12 illustrates an alternate embodiment where it is desirous of providing an ultrasonic dental unit 12a in combination with a fluid supply unit 10a in which a choice is provided in that either an internal supply of fluid is obtained from the reservoir means or an external source of water or fluid is provided. It may be desirous of flushing with water the complete ultrasonic fluid supply and dental system and towards this end external solenoid means 206a is provided having an inflow of water in the direction of arrow 208a therein. The necessary selection is provided by function means 210a which is electrically connected to the relay 104a, fluid solenoid 92a, and external solenoid 206a by leads 211a, 212a and 213a respectively. The function means 210a may be provided on the front panel thereby providing for the user easy means to switch from the internal reservoir to an external source of fluid. In all other respects, when the system is to be made operational the priming and rinsing thereof can still be accomplished as previously described and illustrated.

FIGS. 13 and 14 illustrate an alternate embodiment of the present invention in which the fluid supply unit 10b includes pumping means 82b having an air pump 84b utilized in conjunction with the reservoir means 40b. As illustrated in FIG. 14, the container 42b may have a sealed cap or rubber stopper 214b at one end thereof with the air pump 84b having at one end thereof a pair of spaced apart prongs or piercing elements 215b and 216b adapted to pierce the stopper 214b. Air is pumped through conduit 217b in the direction of arrow 218b into the container 42b to pressurize same and force the fluid therein out through prong 216b and in turn through conduit 219b with the fluid flowing in the direction of arrow 220b. The fluid in conduit 219b is in turn coupled to the dental instrument in the manner as previously illustrated. The fluid supply unit 10b illustrated in FIGS. 13 and 14 simplifies the system in that the fluid solenoid does not have to be utilized and the venting solenoid is also eliminated. Various mechanical means may be provided to assist the piercing by the prongs 215b and 216b through the rubber stopper 214b. Although the container 42b has been illustrated in a horizontal position so that it might be fully enclosed within the cabinet 30b, the vertical positionment permits a full draining of the container more easily.

Accordingly, the present invention may be utilized in conjunction with various professional dental and medical devices that presently utilize tap water during operation thereof. The dental equipment may be comprised of a floor stand that has a dental drill and lavage device extendable therefrom as well as a drinking water spout, all of which may now be provided with a sterile fluid.

Although illustrative embodiments of the invention have been described in detail herein with reference to the accompanying drawings, it is to be understood that the invention is not limited to those precise embodiments, and that various changes and modifications may be effected therein without departing from the scope or spirit of the invention, except as defined in the appended claims.

We claim:
1. An auxiliary fluid supply unit for use in conjunction with a dental or medical instrument having a handpiece including an operative tip adapted for simultaneous activation and supplying of fluid through the handpiece as well as the tip, said fluid supply unit comprising:
   A. dispensing means for pumping fluid and adapted to be coupled to said instrument so that fluid is communicated to the handpiece,
   B. fluid reservoir means communicating with said dispensing means to permit the utilization of a variety of fluids for performing procedures with the instrument,
   C. said dispensing means includes pumping means communicating with said reservoir means for pumping fluid under pressure to said instrument,
   D. remote control means electrically coupling said instrument to said dispensing means for simultaneously energizing the instrument and the auxiliary fluid pumping means and dispensing fluid from said reservoir means by said pumping means through the handpiece, and
   E. said control means including:
      (1) switching means electrically coupled to said instrument and said dispensing means for simultaneous energizing and control thereof,
      (2) remote means operatively connected to said switching means for simultaneously activating the instrument and permitting the flow of fluid therethrough, and
      (3) connecting means between said control means and said instrument for permitting the remote operation of the instrument by activation of said control means.

2. An auxiliary fluid supply unit as in claim 1, and further including venting means operatively associated with said control means and said dispensing means so as to obtain the removal of any entrapped gas therein prior to pumping fluid to the instrument.

3. An auxiliary fluid supply unit as in claim 1, and further including rinsing means operatively associated with said control means and said dispensing means to activate the instrument and said dispensing means to permit a pumping of fluid from said reservoir means for rinsing of the supply unit and the instrument.

4. An auxliary fluid supply unit as in claim 1, wherein the instrument is in the form of an ultrasonic dental prophylaxis unit with an ultrasonically vibratable tip.

5. An auxiliary fluid supply unit as in claim 1, wherein said pumping means is adapted to pump air into said reservoir means for pressurizing same.

6. An auxiliary fluid supply unit as in claim 5, wherein said reservoir means includes a container having a sealed closure at one end thereof and said pumping means includes a pair of elements for piercing said closure, one of said elements adapted for the flow of air into said container to pressurize same with the other of said elements adapted to carry the fluid from said container to the instrument.

7. An auxiliary fluid supply unit as in claim 1, wherein said dispensing means includes hydraulic system means including:
   a. a first valve having inlet and outlet ports, said inlet port connected to said pumping means and said outlet port connected to the instrument, and
   b. a second valve having inlet and outlet ports, said inlet port connected to said pumping means and said outlet port vented to the atmosphere, such that the operator may activate either valve to vent the auxiliary fluid supply unit or pump fluid therefrom to the instrument.

8. An auxiliary fluid supply unit as in claim 7, wherein said pumping means includes a fluid pump having a chamber therein with spaced apart ports connected to the inlet ports of said first valve and said second valve respectively.

9. An auxiliary fluid supply unit as in claim 1, wherein the instrument is in the form of a dental drill unit having a drill bit forming the tip thereof.

10. An auxiliary fluid supply unit for use in conjunction with a dental instrument having a handpiece with a tip adapted to be inserted within the oral cavity and simultaneously supplying fluid through the handpiece, said fluid supply unit comprising:
   A. fluid dispensing means,
   B. fluid reservoir means communicating with said dispensing means to permit the utilization of a variety of fluids for performing oral hygienic procedures with the dental instrument,
   C. fluid coupling means adapted for connecting said fluid dispensing means to the dental instrument so that fluid from said fluid dispensing means is communicated to the dental handpiece,
   D. said dispensing means includes pumping means communicating with said reservoir means for pumping fluid under pressure through said coupling means to the dental instrument,
   E. remote control means electrically connecting the dental instrument with the fluid dispensing means for simultaneously energizing the dental instrument and the auxiliary fluid supply unit such that fluid from said reservoir means is dispensed through the handpiece,
   F. said control means including:
      (1) first switch means electrically connected to the dental instrument and said fluid dispensing means and adapted to be connected to a source of electrical energy, and
      (2) second switch means operatively connected to said first switch means such that activation of said second switch means simultaneously remotely activates the dental instrument to operate the tip thereof and permit the flow of the fluid from said reservoir means therethrough, and
   G. venting means operatively associated with said control means and said dispensing means so as to obtain a flow of atmospheric air as required.

11. An auxiliary fluid supply unit as in claim 10, wherein the dental instrument is in the form of an ultrasonic prophylaxis unit with the tip to be ultrasonically vibrated upon energizing of the dental instrument.

12. An auxiliary fluid supply unit as in claim 10, and further including rinsing means operatively associated with said control means and said dispensing means to activate the dental instrument and said dispensing means to permit a pumping of fluid from said reservoir means for rinsing of the supply unit and the dental instrument.

13. An auxiliary fluid supply unit as in claim 10, wherein the dental instrument is in the form of a dental drill with the drill bit forming the tip thereof.

14. An auxiliary fluid supply unit as in claim 10, wherein said pumping means is adapted to pump air into said reservoir means for pressurizing same.

15. An auxiliary fluid supply unit as in claim 14, wherein said reservoir means includes a container having a sealed closure at one end thereof and said pumping means includes a pair of elements for piercing said closure, one of said elements adapted for the flow of air ito said container to pressurize same with the other of said elements adapted to carry the fluid from said container to said coupling means.

16. An auxiliary fluid supply unit as in claim 10, wherein said fluid dispensing means includes a hydraulic system means including:
   a. a first valve having inlet and outlet ports, said inlet port connected to said pumping means and said outlet port connected to said coupling means, and
   b. a second valve having inlet and outlet ports, said inlet port connected to said pumping means and said outlet port vented to the atmosphere, such that the operator may activate either valve to vent the auxiliary fluid supply unit or pump fluid therefrom to the dental instrument.

17. An auxiliary fluid supply unit for use in conjunction with a dental instrument having a handpiece with a tip adapted to be inserted within the oral cavity and simultaneously supplying fluid through the handpiece, said fluid supply unit comprising:
   A. fluid dispensing means,
   B. fluid reservoir means communicating with said dispensing means to permit the utilization of a variety of fluids for performing oral hygienic procedures with the dental instrument,
   C. fluid coupling means adapted for connecting said fluid dispensing means to the dental instrument so that fluid from said fluid dispensing means is communicated to the dental handpiece,
   D. remote control means electrically connecting the dental instrument with the fluid dispensing means for simultaneously energizing the dental instrument and the auxiliary fluid supply unit such that fluid from said reservoir means is dispensed through the handpiece upon activation of the dental instrument,
   E. said dispensing means including pumping means communicating with said reservoir means for pumping fluid under pressure through said coupling means to the dental instrument,
   F. said fluid dispensing means including a hydraulic system means including:
      (1) a first valve having inlet and outlet ports, said inlet port connected to said pumping means and said outlet port connected to said coupling means, and
      (2) a second valve having inlet and outlet ports, said inlet port connected to said pumping means and said outlet port vented to the atmosphere,
      (3) switching means to enable the operator to activate either said first or said second valve to vent the auxiliary fluid supply unit or to pump fluid therefrom to the dental instruments, and
   G. said switching means including a means for providing a first normally open electrical signal path and a means for selectively providing an additional one of two electrical signal paths.

18. An auxiliary fluid supply unit as in claim 17, wherein said pumping means includes a fluid pump having a chamber therein with spaced apart ports connected to the inlet ports of said first valve and said second valve respectively.

19. An auxiliary fluid supply unit as in claim 17, wherein said fluid coupling means includes a conduit member adapted to be removably secured to the dental instrument.

20. An auxiliary fluid supply unit as in claim 19, wherein said conduit member is also adapted to be removably secured to the auxiliary fluid supply unit.

21. An auxiliary fluid supply unit as in claim 17, wherein said control means includes:
   a. first switch means electrically connected to the dental instrument and said fluid dispensing means and adapted to be connected to a source of electrical energy, and
   b. second switch means operatively connected to said first switch means such that activation of said second switch means simultaneously remotely activates the dental instrument to permit the flow of the fluid from said reservoir means therethrough.

22. An auxiliary fluid supply unit as in claim 21, wherein said second switch means includes a footswitch for activating said first switch means.

23. An auxiliary fluid supply unit as in claim 21, and further including rinsing switch means coupled to said first switch means for activating said first means.

24. An auxiliary fluid supply unit as in claim 21, and further including energizing means coupled to said first switch means for powering the fluid supply unit.

25. An auxiliary fluid supply unit as in claim 17, and further including external fluid supply means operatively associated with said fluid coupling means and said remote control means so as to provide the user with the option to select fluid from said reservoir means or an external source.

26. An auxiliary fluid supply unit for use in conjunction with a dental instrument having a handpiece with a tip adapted to be inserted within the oral cavity and simultaneously supplying fluid through the handpiece, said fluid supply unit comprising:
   A. fluid dispensing means including pumping means,
   B. fluid reservoir means adapted to be readily engaged and interchangeable with said fluid dispensing means and communicating with said pumping means to permit the utilization of a variety of fluids for performing oral hygienic procedures with the dental instrument, said pumping means is adapted to pump air into said reservoir means for pressurizing same, said reservoir means includes a container having a sealed closure at one end thereof and said pumping means includes a pair of elements for piercing said closure, one of said elements adapted for the flow of air into said container to pressurize same with the other of said elements adapted to carry the fluid from said container,
   C. fluid coupling means adapted for connecting said fluid carrying element from said container to the dental instrument so that fluid from said fluid dispensing means is communicated to the dental handpiece,
   D. remote control means for electrically connecting the dental instrument with the fluid dispensing means for operation of the dental instrument and the auxiliary fluid supply unit in order to dispense fluid through the handpiece,
   E. said control means including:
   (1) first switch means electrically connected to the dental instrument and said fluid dispensing means and adapted to be connected to a source of electrical energy,
- (2) second switch means operatively connected to said first switch means such that activation of said second switch means simultaneously remotely activates the dental instrument and permits the flow of the fluid from said reservoir means therethrough, and
- (3) said second switch means including a footswitch for activating said first switch means.

27. An auxiliary fluid supply unit as in claim 26, wherein the dental instrument is an ultrasonic prophylaxis unit with the tip to be ultrasonically vibrated upon energizing of the dental instrument.

28. An auxiliary fluid supply unit as in claim 27, wherein the dental instrument is in the form of a dental drill with the drill bit forming the tip thereof.

29. A fluid supply unit to remotely activate and control the flow of fluid within a dental instrument comprised of a power supply with fluid control valve and a handpiece with a tip to be inserted within the oral cavity for simultaneously supplying fluid and power from the power supply to the handpiece for operating the tip and providing fluid adjacent the work site, said fluid supply unit comprising:
- A. fluid coupling means adapted for connecting the fluid supply unit to the dental instrument so that fluid is communicated through the fluid control valve to the dental handpiece, said fluid coupling means including a conduit member adapted to be removably secured to the dental instrument,
- B. fluid reservoir means adapted to permit the utilization of a variety of fluids for performing oral hygienic procedures with the dental instrument,
- C. fluid dispensing means operatively associated with said coupling means and said reservoir means, said fluid dispensing means including:
  - (1) pumping means communicating with said fluid reservoir means for pumping fluid from said reservoir means, and
  - (2) hydraulic system means including:
    - (i) a first valve having inlet and outlet ports, said inlet port connected to said pumping means and said outlet port connected to said coupling means, and
    - (ii) a second valve having inlet and outlet ports, said inlet port connected to said pumping means and said outlet port vented to the atmosphere, such that the operator may sequentially activate either of said valves to first vent the fluid supply unit and then pump fluid therefrom to the dental instrument,
- D. control means for electrically connecting the dental instrument to the fluid dispensing means so as to remotely operate the dental instrument and the fluid supply unit, said control means including:
  - (1) first switch means electrically connected to the dental instrument and said first and second valves of said fluid dispensing means and adapted to be connected to a source of electrical energy, and
  - (2) second switch means operatively connected to said first switch means such that activation of said second switch means simultaneously remotely activates the dental instrument to obtain power from the power supply to operate the tip extending from the handpiece and opens the fluid control valve to permit the flow of the fluid therethrough.
- E. said pumping means including a fluid pump having a chamber therein with spaced apart ports connected to the input ports of said first valve and said second valve respectively, and
- F. energizing means coupled to said first switch means for powering the fluid supply unit independently of the dental instrument.

30. A fluid supply unit as in claim 29, and further including rinsing switch means operatively associated with said first switch means of said control means to simultaneously activate the dental instrument and said fluid dispensing means to permit a rinsing of the supply unit and the dental instrument.

31. A fluid supply unit as in claim 29, wherein the dental instrument is an ultrasonic prophylaxis unit adapted to vibrate the tip.

32. A fluid supply unit as in claim 29, wherein the dental instrument is in the form of a dental drill.

33. A fluid supply unit as in claim 29, wherein said fluid coupling means includes a conduit member adapted to be removably secured to the fluid supply unit.

34. A fluid supply unit as in claim 29, wherein said second switch means includes a footswitch for activating said first switch means.

35. A fluid supply unit to remotely activate and control the flow of fluid within a dental instrument comprised of a power supply with fluid control valve and a handpiece with a tip adapted to be inserted within the oral cavity for simultaneously supplying fluid and power from the power supply to the handpiece for operating the tip and providing fluid adjacent the work site, said fluid supply unit comprising:
- A. fluid coupling means adapted for connecting the fluid supply unit to the dental instrument so that fluid is communicated through the fluid control valve to the dental handpiece,
- B. fluid reservoir means adapted to permit the utilization of a variety of fluids for performing oral hygienic procedures with the dental instrument,
- C. fluid dispensing means operatively associated with said coupling means and said reservoir means, said fluid dispensing means including:
  - (1) pumping means communicating with said fluid reservoir means for pumping fluid from said reservoir means, and
  - (2) hydraulic system means including:
    - (i) a first valve having inlet and outlet ports, said inlet port connected to said pumping means and said outlet port connected to said coupling means, and
    - (ii) a second valve having inlet and outlet ports, said inlet port connected to said pumping means and said outlet port vented to the atmosphere, such that the operator may sequentially activte either of said valves first to vent the fluid supply unit and then to pump fluid therefrom to the dental instrument, and
- D. control means for electrically connecting the dental instrument to the fluid dispensing means for remote operation of the dental instrument and the fluid supply unit, said control means including:
  - (1) first switch means electrically connected to the dental instrument and said first and second valves of said fluid dispensing means and adapted to be connected to a source of electrical energy, (2) second switch means operatively connected to said first switch means such that activation of said second switch means remotely activates the dental instrument to obtain power from the power supply to operate the handpiece and simultaneously opens the fluid control valvue to permit the flow of the fluid therethrough, and (3) said first switch means including a means for providing a first normally open electrical signal path and a means for selectively providing an additional one of two electrical signal paths.

36. A fluid supply unit as in claim 35, and further including external fluid supply means operatively associated with said fluid coupling means and said control means so as to provide the user with the option to select fluid from said reservoir means or said external source.

37. A fluid supply unit as in claim 35, and further including housing means with said fluid coupling means, said fluid reservoir means, said fluid dispensing means and said control means mounted in operative relationship thereto.

38. A fluid supply unit for remote activation and control of the flow of fluid within a dental instrument comprised of a power supply with fluid control valve and a handpiece with a tip adapted to be inserted within the oral cavity for simultaneously supplying fluid and power from the power supply to the handpiece for operating the tip and providing fluid adjacent the work site, said fluid supply unit comprising:

A. housing means,

B. fluid reservoir means adapted to be removably mounted relative to said housing means to permit employment of a variety of fluids for performing oral hygienic procedures with the dental instrument, C. fluid coupling means adapted for connecting said fluid reservoir means to the dental instrument so that fluid is dispensed to the dental handpiece, D. fluid dispensing means mounted within said housing means and operatively associated with said reservoir means and said coupling means, said dispensing means including:

(1) pumping means, and (2) hydraulic system means including:

(i) a first valve having inlet and outlet ports, said inlet port connected to said pumping means and said outlet port connected to said fluid coupling means, and (ii) a second valve having inlet and outlet ports, said inlet port connected to said pumping means and said outlet port vented to the atmosphere, such that the operator may activate either valve to vent the auxiliary fluid supply unit or pump fluid therefrom to the dental instrument, and E. control means mounted within said housing means and controllable exteriorally therefrom for electrically connecting the dental instrument with the fluid dispensing means for remote operation of the dental instrument and the auxiliary fluid supply unit, said control means including:

(1) switch means electrically connected to the dental instrument and said fluid dispensing means and adapted to be connected to a source of electrical energy, and (2) footswitch means operatively connected to said switch means from said housing means, such that activation of said footswitch means simultaneously activates the dental instrument to obtain power from the power supply for operating the handpiece, opens said first valve, and activates said pumping means to permit the flow of the fluid from said reservoir means therethrough, (3) rinsing switch means coupled to said switch means and mounted on said housing for manual engagement by the operator to open said first valve, and activate said pumping means so as to flush the dental instrument and (4) prime switch means coupled to said switch means and mounted on said housing means for manual engagement by the operator to open said second valve and simultaneously activate said pumping means until any air entrapped therein is first dispensed.

39. An auxiliary fluid supply unit as in claim 38, and further including energizing means coupled to said switch means and mounted on said housing means for manual engagement by the operator for powering the fluid supply unit.

40. An auxiliary fluid supply unit as in claim 38, wherein said switch means includes a relay having a normally open circuit means and a single pole two position circuit means.

41. A fluid supply unit as in claim 38, wherein said pumping means includes a fluid pump having a chamber therein with spaced apart ports connected to the inlet ports of said first valve and said second valve respectively.

42. A fluid supply unit as in claim 38, wherein said fluid coupling means further includes a conduit member adapted to be removably secured to the dental instrument.

43. A fluid supply unit as in claim 42, wherein said conduit member is also adapted to be removably secured to the fluid supply unit.

44. An auxiliary supply unit as in claim 1 wherein said fluid supply unit is a liquid supply unit and said fluid is a liquid.

45. An auxiliary supply unit as in claim 1 further comprising valve means intervening between said reservoir means and said handpiece and wherein said valve means is activated simultaneously with said instrument and said dispensing means.

46. An auxiliary supply unit as in claim 1 for use in conjunction with a dental or medical instrument which has instrument valve means, further comprising pump valve means and wherein said instrument valve means and said pump valve means are activated simultaneously with activation of said instrument.

* * * * *